(12) United States Patent
Ridden et al.

(10) Patent No.: US 10,517,835 B2
(45) Date of Patent: Dec. 31, 2019

(54) COMPOSITION AND METHODS OF TREATMENT (71) Applicant: Blueberry Therapeutics Limited, Macclesfield, Cheshire (GB)

(72) Inventors: John Ridden, Macclesfield (GB); Christine Caroline Ridden, Macclesfield (GB); David Cook, Macclesfield (GB)

(73) Assignee: Bueberry Therapeutics Limited, Macclesfield, Cheshire (GB)

( * ) Notice: Subject to any disclaimer, the term of this patent is extended or adjusted under 35 U.S.C. 154(b) by 0 days.

(21) Appl. No.: 15/741,924

(22) PCT Filed: Jul. 6, 2016

(86) PCT No.: PCT/GB2016/052031
§ 371 (c)(1),
(2) Date: Jan. 4, 2018

(87) PCT Pub. No.: WO2017/006112
PCT Pub. Date: Jan. 12, 2017

(65) Prior Publication Data
US 2018/0193281 A1   Jul. 12, 2018

(30) Foreign Application Priority Data
Jul. 6, 2015 (GB) .................................. 1511799.7

(51) Int. Cl.
*A61K 9/51* (2006.01)
*A61K 9/00* (2006.01)
*A61K 9/70* (2006.01)
*A61K 31/137* (2006.01)
*A61M 37/00* (2006.01)

(52) U.S. Cl.
CPC .......... *A61K 9/5146* (2013.01); *A61K 9/0021* (2013.01); *A61K 9/7084* (2013.01); *A61K 31/137* (2013.01); *A61M 37/0015* (2013.01); *A61M 2037/0023* (2013.01); *A61M 2037/0061* (2013.01)

(58) Field of Classification Search
None
See application file for complete search history.

(56) References Cited

U.S. PATENT DOCUMENTS

| 5,681,849 | A | * | 10/1997 | Richter | A61K 9/0014 514/481 |
|---|---|---|---|---|---|
| 2007/0190160 | A1 | * | 8/2007 | Turos | A61K 9/5138 424/490 |
| 2008/0161405 | A1 | * | 7/2008 | Xia | A61K 9/0014 514/635 |
| 2010/0197804 | A1 | * | 8/2010 | Hirsch | A61K 9/2009 514/741 |

FOREIGN PATENT DOCUMENTS

| WO | WO-2015/044669 A1 | 4/2015 | |
| WO | WO-2015044669 A1 * | 4/2015 | ........... A61K 9/0014 |

OTHER PUBLICATIONS

Gustavo F. de Paula, Germano I. Netto and Luiz Henrique C. Mattoso. Physical and Chemical Characterization of Poly(hexamethylene biguanide) Hydrochloride. Polymers 2011, 3, 928-941. (Year: 2011).*
Hofmueller, W. et al., "Keratomycosis refractory to common therapy due to a Coelomycete not yet described treated successfully with PHMB in combination with systemic and local terbinafine. A case report.", Mycoses, $18^{th}$ Congress of the International Society for Human and Animal Mycology, vol. 55(4):207, Jun. 2012.
International Search Report, dated Sep. 23, 2016, issued on International Patent Application No. PCT/GB2016/052031.

* cited by examiner

*Primary Examiner* — Michael P Cohen
(74) *Attorney, Agent, or Firm* — Howson & Howson LLP (57) ABSTRACT

The present invention relates to a composition comprising nanoparticles formed of a polymer and terbinafine, wherein the nanoparticles comprise particles in the range of 0.5 to 5 nm and/or in the range of 150 to 250 nm. Such compositions are particularly suited, but not limited, to the treatment of fungal nail infections.

16 Claims, 9 Drawing Sheets

Sample video frame

FIG. 7E 60.0 µg/ml terbinafine

FIG. 7D 6.00 µg/ml terbinafine

FIG. 7C 0.60 µg/ml terbinafine

FIG. 7B 0.06 µg/ml terbinafine

FIG. 7A Control (ddH2O)

COMPOSITION AND METHODS OF TREATMENT

TECHNICAL FIELD OF THE INVENTION

The invention relates to a composition (and methods of producing such compositions) comprising nanoparticles formed of a polymer and terbinafine, wherein the nanoparticles comprise particles in the range of 0.5 to 5 nm and/or in the range of 150 to 250 nm. Such compositions are particularly suited, but not limited, to the treatment of fungal nail infections.

BACKGROUND TO THE INVENTION

Fungal infections are increasingly common in both human and animals, yet the treatment of such infections remains problematic due to toxicity of the antifungal compositions, poor solubility of these compositions and the remote location of some infections which can prove difficult to reach using traditional medicinal formulations.

A broad spectrum of antifungals such as amphotericin B, hamycin, filipin and nystatin were discovered in 1960s. But due to toxicity only hamycin and nystatin are used topically and amphotericin B systemically. A breakthrough in antifungal therapy was the introduction of azoles especially ketoconazole. The major classes of antifungals currently used are polyenes, azoles allyl amines, lipopeptides, and pyrimidines. However, polyenes are toxic to mammalian cells. Azoles are well tolerated topically but have side effects when given systemically and there have been several reports of resistance to azoles. Flucytosin is the most common pyrimidine used. Whilst it has excellent tissue penetration, resistance against flucytosine can develop rapidly and produce gastro intestinal side effects. Lipopetides display low toxicity and several trials are still on going to test efficacy.

The development of new antifungals is constrained because fungi are eukaryotic and cellular targets, if disrupted, can also damage host cells. The increase in fungal infections and increase in use of antifungals has resulted in emergence of resistance among fungi. Anti-fungal resistance has high clinical impact as fungal diseases are causing an increase in morbidity and mortality of immunocompromised patients.

It is estimated that around 40% of newly discovered drugs fail due to lack of proper delivery because of aqueous solubility problems. In the case of topical delivery of drugs, the barrier properties of skin often require permeation enhancers to achieve the required dose of drugs.

Onychomycosis (more commonly known as fungal nail infection) causes nails to thicken, discolor, disfigure, and split. Without treatment, the nails can become so thick that they press against the inside of shoes, causing pressure, irritation, and pain. There are risks for further complications especially in patients with diabetes, those with peripheral vascular disease and the immunocompromised patient. Fungal nail infection may cause psychological and social problems. The incidence of fungal nail infection increases with age and has a prevalence of ~30% of the over 60 s with significant incidence in Europe with even higher levels in Asia. Fungal nail infection may affect one or more toenails and/or fingernails and can completely destroy the nail if left untreated.

The current treatment for fungal nail infection is as topical nail lacquer/paint (such as amorolfine) 1-2 times per week for 6-12 months and/or oral antifungals (such as terbinafine or itraconazole). Oral antifungals can have severe side effects such as gastro-intestinal upset and can even result in liver failure. Relapse is commonly reported in 25-50% of cases and many patients will not commit to the treatment course due to predicted side effects and length of treatment time and often only when disease becomes more aggressive will treatment begin. Current oral or topical treatments can take 6-12 months to work. Oral treatments have to saturate the systemic circulation to reach the toes and the increased doses increases the risk to the gastro-intestinal and liver complications. Topical treatments are ineffective at penetrating the thickened nail and again require high dosing.

Athlete's Foot (otherwise known as ringworm of the foot, Tinea pedis or moccasin foot) is a fungal infection of the skin generally caused by fungi in the genus *Trichophyton* (most commonly *T. rubrum* or *T. mentagrophytes*). The various parasitic fungi that cause athelete's foot also can cause other skin infection such as onychomycosis and Tinea cruris. Whilst distinct from fungal nail infection, athelete's foot also has issue with compliance and duration of treatment.

Fungal keratitis is the inflammation of the cornea caused by a fungal infection. Natamycin ophthalmic suspension is often used for filamentous fungal infection, whereas Fluconazole ophthalmic solution is recommended for *Candida* infections. Amphotericin B eye drops are used for difficult to treat cases, however, these eye drops can be toxic in an individual.

Oral candidiasis is a fungal infection of the mucous membranes of the mouth by *Candida* species. It can be particularly problematic in immuno-deficient patients where it is often difficult to treat successfully.

WO2015044669 discloses a topical composition (and methods of producing such compositions) for the treatment of a fungal infection comprising a polymer capable of forming nanoparticles and an antifungal agent.

An object of the present invention is to address one or more of the above problems associated with current antifungal treatments. It is also an object of the present invention to provide a topical anti-fungal treatment. It is additionally an object of the present invention to provide a treatment which allows for better penetration of the anti-fungal agent through a number of body tissues, such as the nail and/or dermis, mucosal membranes, cornea and/or sclera.

SUMMARY OF THE INVENTION

In accordance with an aspect, there is provided a composition comprising nanoparticles formed of a polymer and terbinafine, wherein the nanoparticles comprise particles in the range of 0.5 to 5 nm and/or in the range 150 to 250 nm.

The nanoparticles may be present in at least two distinct particle sizes groups comprising:
a) a first species in the range of 0.5 to 5 nm; and
b) a second species in the range of 150 to 250 nm.

In accordance with a further aspect, there is provided a composition comprising nanoparticles formed of a polymer and terbinafine, wherein the nanoparticles are present in at least two distinct particle size groups.

The nanoparticles may be present in at least two distinct particle sizes groups comprising:
a) a first species in the range of 0.5 to 5 nm; and
b) a second species in the range of 150 to 250 nm.

Preferably, the particles in the first species are in the range of 0.5 to 3 nm. More preferably, the particles in the first species are in the range of 0.5 to 2.5 nm. Most preferably, the particles in the first species are in the range of 0.5 to 2 nm. Preferably, the particles in the second species are in the range of 150 to 225 nm. More preferably, the particles in the second species are in the range of 150 to 220 nm. Most preferably, the particles in the second species are in the range of 150 to 215 nm.

Preferably, the average size of the particles in the first species will be in the range of 0.5 to 1.5 nm. More preferably, the average size of the particles in the first species will be in the range of 0.6 to 1.4 nm. Even more preferably, the average size of the particles in the first species will be in the range of 0.7 to 1.2 nm. Most preferably, the average size of the particles in the first species will be in the region of about 0.9 nm.

Preferably, the average size of the second species of particles will be in the range of 150 to 225 nm. More preferably, the average size of the second species of particles will be in the range of 155 to 220 nm. Even more preferably, the average size of the second species of particles will be in the range of 160 to 215 nm. Most preferably, the average size of the second species of particles will be in the region of about 160 to about 176 nm.

Preferably, the average modal size of the second species of particles will be in the range of 150 to 225 nm. More preferably, the average modal size of the second species of particles will be in the range of 155 to 220 nm. Even more preferably, the average modal size of the second species of particles will be in the range of 160 to 215 nm. Most preferably, the average modal size of the second species of particles will be in the region of about 164 to about 211 nm.

By forming nanoparticles of generally two (or more) distinct particle size groups, the inventors have found advantageously that, terbinafine is able to penetrate cells much more efficiently. The inventors have further found that the nanoparticle formulations enhances the penetration of terbinafine through human nail. Terbinafine can therefore be formulated into a medicaments having not only an extended release profile, but also employing a reduced therapeutic dose which can be effectively delivered locally rather than systemically thus removing the danger of some orally administered this antifungal agent. By combining a safe nanopolymer delivery system with a potent antifungal agent, it is envisaged that topical treatment can be provided that can improve efficacy and potentially reduce current treatment timelines for infections from 6 months to 6 weeks.

The term "topical" is intended to mean an exterior surface of the body surface, such as skin, nails, eyes, bronchioles, mucosal membranes, mouth and gastrointestinal tract.

The term "terbinafine" is intended to mean the pharmaceutically active substance terbinafine hydrochloride which is a synthetic allylamine antifungal originally marketed under the trade name Lamisil®. The term is also intended to include pharmaceutical variations of terbinafine hydrochloride such as non-toxic organic, or inorganic, acid, or base, addition salt, in a pharmaceutically acceptable form.

The measurement of the size/diameter of the nanoparticles is preferably conducted using dynamic light scattering analysis.

In accordance with a further aspect, there is provided a composition comprising nanoparticles formed of a polymer and an antifungal agent, wherein the nanoparticles are present as:
a) a first species in the range of 0.5 to 5 nm; and
b) a second species in the range of 150 to 250 nm.

The term "antifungal agent" with respect to this aspect is intended to cover a range of compounds and molecules which are capable of inhibiting growth and/or survival of fungi causing a fungal infection. The antifungal agent employed in conjunction with this aspect will of course be largely governed by its efficacy against the fungi causing the infection. The antifungal agent may comprise one or more agents selected from the following group: Nystatin, Terbinafine, Ketoconazole, Amphotericin B, Itraconazole or Berberine. It is preferred that the antifungal agent comprises terbinafine.

In all aspects, it is preferred that the polymer comprises a linear and/or branched or cyclic polymonoguanide/polyguanidine, polybiguanide, analogue or derivative thereof. The linear and/or branched or cyclic polymonoguanide/polyguanidine, polybiguanide, analogue or derivative thereof may be according to the following formula 1a or formula 1b, with examples provided in tables A and B below:

wherein:

"n", refers to number of repeating units in the polymer, and n can vary from 2 to 1000, for example from 2 or 5 to 10, 20, 30, 40, 50, 60, 70, 80, 90, 100, 150, 200, 250, 300, 350, 400, 450, 500, 600, 700, 800 or 900;

$G_1$ and $G_2$ independently represent a cationic group comprising biguanide or guanidine, wherein $L_1$ and $L_2$ are directly joined to a Nitrogen atom of the guanide. Thus, the biguanide or guanidine groups are integral to the polymer backbone. The biguanide or guanidine groups are not side chain moieties in formula 1a.

Example of cationic groups:

In the present invention, $L_1$ and $L_2$ are the linking groups between the $G_1$ and $G_2$ cationic groups in the polymer. $L_1$ and $L_2$ can independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, —$C_{20}$, —$C_{30}$, —$C_{40}$, —$C_{50}$, —$C_{60}$, —$C_{70}$, —$C_{80}$, —$C_{90}$, —$C_{100}$, —$C_{110}$, —$C_{120}$, —$C_{130}$ or —$C_{140}$, alkyl; or $L_1$ and $L_2$ can (independently) be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, —$C_{20}$, —$C_{30}$, —$C_{40}$, —$C_{50}$, —$C_{60}$, —$C_{70}$, —$C_{80}$, —$C_{90}$, —$C_{100}$, —$C_{110}$, —$C_{120}$, —$C_{130}$ or —$C_{140}$), cycloaliphatic, heterocyclic, aromatic, aryl, alkylaryl, arylalkyl, oxyalkylene radicals, or $L_1$ and $L_2$ can (independently) be a polyalkylene radical optionally interrupted by one or more, preferably one, oxygen, nitrogen or sulphur atoms, functional groups as well as saturated or unsaturated cyclic moiety. Examples of suitable $L_1$ and $L_2$ are groups are listed in table A.

$L_1$, $L_2$, $G_1$ and $G_2$ may have been modified using aliphatic, cycloaliphatic, heterocyclic, aryl, alkaryl, and oxyalkylene radicals.

N and $G_3$ are preferably end groups. Typically the polymers of use in the invention have terminal amino (N) and cyanoguanidine ($G_3$) or guanidine ($G_3$) end groups. Such end groups may be modified (for example with 1,6-diaminohexane, 1,6 di(cyanoguanidino)hexane, 1,6-diguanidinohexane, 4-guanidinobutyric acid) by linkage to aliphatic, cycloaliphatic heterocyclic, heterocyclic, aryl, alkylaryl, arylalkyl, oxyalkylene radicals. In addition, end groups may be modified by linkage to receptor ligands, dextrans, cyclodextrins, fatty acids or fatty acid derivatives, cholesterol or cholesterol derivatives or polyethylene glycol (PEG). Optionally, the polymer can end with guanidine or biguanide or cyanoamine or amine or cyanoguanidine at N and $G_3$ positions or cyanoamine at N and cyanoguanidine at $G_3$ position or guanidine at N and Cyanoguanide at $G_3$ positions or $L_1$ amine at $G_3$ and cyanoguanidine at N. $G_3$ can be $L_1$-amine, $L_2$-cyanoguanidine or $L_2$-guanidine. Depending on the number of polymerization (n) or polymer chain breakage and side reactions during synthesis, heterogeneous mixture of end groups can arise as described above as an example. Thus, the N and G3 groups can be interchanged/present as a heterogeneous mixture, as noted above. Alternatively N and $G_3$ may be absent and the polymer may be cyclic, in which case the respective terminal $L_1$ and $G_2$ groups are linked directly to one another.

In formula 1b, X can be either present or absent. $L_3$, $L_4$ and X are as noted above for "$L_1$ or $L_2$". In Thus, $L_3$ and $L_4$ and X are the linking groups between the $G_4$ and $G_5$ cationic groups in the polymer. $L_3$ and $L_4$ and X can independently represent an aliphatic group containing $C_1$-$C_{140}$ carbon atoms, for example an alkyl group such as methylene, ethylene, propylene, $C_4$, $C_5$, $C_6$, $C_7$, $C_8$, $C_9$ or $C_{10}$; $C_1$-$C_{10}$, $-C_{20}$, $-C_{30}$, $-C_{40}$, $-C_{50}$, $-C_{60}$, $-C_{70}$, $-C_{80}$, $-C_{90}$, $-C_{100}$, $-C_{110}$, $-C_{120}$, $-C_{130}$ or $-C_{140}$, alkyl; or $L_3$ and $L_4$ and X can independently be $C_1$-$C_{140}$ (for example $C_1$, $C_2$, $C_3$, $C_4$, $C_5$, $C_6$, $C_7$, $C_8$, $C_9$ or $C_{10}$; $C_1$-$C_{10}$, $-C_{20}$, $-C_{30}$, $-C_{40}$, $-C_{50}$, $-C_{60}$, $-C_{70}$, $-C_{80}$, $-C_{90}$, $-C_{100}$, $-C_{110}$, $-C_{120}$, $-C_{130}$ or $-C_{140}$), cycloaliphatic, heterocyclic, aromatic, aryl, alkylaryl, arylalkyl, oxyalkylene radicals, or $L_3$ and $L_4$ and X can independently be a polyalkylene radical optionally interrupted by one or more, preferably one, oxygen, nitrogen or sulphur atoms, functional groups as well as saturated or unsaturated cyclic moiety. Examples of suitable $L_3$ and $L_4$ and X are groups are listed in table B.

"$G_4$" and "$G_5$" are cationic moieties and can be same or different. At least one of them is a biguanidine moiety or carbamoylguanidine, and the other moiety may be as above (biguanidine or carbamoylguanidine) or amine. For the avoidance of doubt, in formula 1b, cationic moiety $G_4$ and $G_5$ do not contain only single guanidine groups. For example, $G_4$ and $G_5$ typically do not contain single guanidine groups. Examples of such compounds are polyallylbiguanide, poly(allylbiguanidnio-co-allylamine), poly(allylcarbamoylguanidino-co-allylamine), polyvinylbiguanide, as listed in table B.

Example of polyallylbiguanide is as shown below:

In case of polyallylbigunidine $L_3$ and $L_4$ are identical, $G_4$ and G5 are similar, thus polyallylbiguanide can be simplified as below.

Example of poly(allylcarbamoylguanidnio-co-allylamine) is as shown below

The polymers for use in the invention will generally have counter ions associated with them. Suitable counter ions include but are not limited to the following: halide (for example chloride), phosphate, lactate, phosphonate, sulfonate, amino carboxylate, carboxylate, hydroxy carboxylate, organophosphate, organophosphonate, organosulfornate and organosuflate.

Polymers for use in the invention can be either heterogeneous mixtures of polymers of different "n" number or homogenous fractions comprising specified "n" numbers purified by standard purification methods. As indicated above the polymers may also be cyclic and in addition may be branched.

Preferred numbers for "n" include 2-250, 2-100, 2-80 and 2-50.

TABLE A

Examples of polymer analogues arising from formula 1a.

| Name | $L_1$ | $G_1$ | $L_2$ | $G_2$ |
| --- | --- | --- | --- | --- |
| Polyhexamethylene biguanide (PHMB) | $(CH_2)_6$ | Biguanide | $(CH_2)_6$ | Biguanide |
| Polyethylene biguanide (PEB) | $(CH_2)_2$ | Biguanide | $(CH_2)_2$ | Biguanide |
| Polyethylenetetramethylene biguanide | $(CH_2)_2$ | Biguanide | $(CH_2)_4$ | Biguanide |
| Polyethylene hexamethylene biguanide (PEHMB) | $(CH_2)_2$ | Biguanide | $(CH_2)_6$ | Biguanide |
| Polypropylene biguanide, Polyaminopropyl biguanide (PAPB) | $(CH_2)_3$ | Biguanide | $(CH_2)_3$ | Biguanide |
| Poly-[2-(2-ethoxy)-ethoxyethyl]-biguanide-chloride] (PEEG) | $(CH_2CH_2OCH_2CH_2OCH_2CH_2)$ | Biguanide | $(CH_2CH_2OCH_2CH_2OCH_2CH_2)$ | Biguanide |

TABLE A-continued

Examples of polymer analogues arising from formula 1a.

| Name | $L_1$ | $G_1$ | $L_2$ | $G_2$ |
|---|---|---|---|---|
| Polypropylenehexamethylene biguanide | $(CH_2)_3$ | Biguanide | $(CH_2)_6$ | Biguanide |
| Polyethyleneoctamethylene biguanide | $(CH_2)_2$ | Biguanide | $(CH_2)_8$ | Biguanide |
| Polyethylenedecamethylene biguanide | $(CH_2)_2$ | Biguanide | $(CH_2)_{10}$ | Biguanide |
| Polyethylenedodecamethylene biguanide | $(CH_2)_2$ | Biguanide | $(CH_2)_{12}$ | Biguanide |
| Polytetramethylenehexamethylene biguanide | $(CH_2)_4$ | Biguanide | $(CH_2)_6$ | Biguanide |
| Polytetramethylenebiguanide | $(CH_2)_4$ | Biguanide | $(CH_2)_4$ | Biguanide |
| Polypropyleneoctamethylene biguanide | $(CH_2)_3$ | Biguanide | $(CH_2)_8$ | Biguanide |
| Polytetramethyleneoctamethylene Biguanide | $(CH_2)_4$ | Biguanide | $(CH_2)_8$ | Biguanide |
| Polyhexamethylene diethylenetriamine biguanide | $(CH_2)_6$ | Biguanide | $CH_2-CH_2-NH-CH_2-CH_2$ | Biguanide |
| Polyhexamethylene guanide (PHMG) | $(CH_2)_6$ | guanidine | $(CH_2)_6$ | guanidine |
| Polyethylene guanide | $(CH_2)_2$ | guanidine | $(CH_2)_2$ | guanidine |
| Polyethylenetetramethylene guanide | $(CH_2)_2$ | guanidine | $(CH_2)_4$ | guanidine |
| Polyethylene hexamethylene guanide | $(CH_2)_2$ | guanidine | $(CH_2)_6$ | guanidine |
| Polypropylene guanide, Polyaminopropyl guanide (PAPB) | $(CH_2)_3$ | guanidine | $(CH_2)_3$ | guanidine |
| Poly-[2-(2-ethoxy)-ethoxyethyl]-guanide | $(CH_2CH_2OCH_2CH_2OCH_2CH_2)$ | guanidine | $(CH_2CH_2OCH_2CH_2OCH_2CH_2)$ | guanidine |
| Polypropylenehexamethylene guanide | $(CH_2)_3$ | guanidine | $(CH_2)_6$ | guanidine |
| Polyethyleneoctamethylene guanide | $(CH_2)_2$ | guanidine | $(CH_2)_8$ | guanidine |
| Polyethylenedecamethylene guanide | $(CH_2)_2$ | guanidine | $(CH_2)_{10}$ | guanidine |
| Polyethylenedodecamethylene guanide | $(CH_2)_2$ | guanidine | $(CH_2)_{12}$ | guanidine |
| Polytetramethylenehexamethylene guanide | $(CH_2)_4$ | guanidine | $(CH_2)_6$ | guanidine |
| Polypropyleneoctamethylene guanide | $(CH_2)_3$ | guanidine | $(CH_2)_8$ | guanidine |
| Polytetramethylene guanide | $(CH_2)_4$ | guanidine | $(CH_2)_4$ | guanidine |
| Polyhexamethylene diethylenetriamine guanide | $(CH_2)_6$ | guanidine | $CH_2-CH_2-NH-CH_2-CH_2$ | guanidine |

| Polymer | CAS Number |
|---|---|
| Polyhexamethylene biguanide hydrochloride (PHMB) | 27083-27-8 32289-58-0 |
| Polyhexamethylene guanidine hydrochloride (PHMG) | 57028-96-3 |
| Poly-[2-(2-ethoxy)-ethoxyethyl]-guanidinium-chloride] (PEEG) | 374572-91-5 |

CAS numbers for example compounds arising from formula 1a

TABLE B

Examples of polymer analogues arising from formula 1b.

| Name | $L_3$ | $G_4$ | $L_4$ | $G_5$ | x |
|---|---|---|---|---|---|
| Polyallylbiguanide | $(CH_2-CH)$ | Biguanide | $(CH_2-CH)$ | Biguanide | $CH_2$ |
| poly(allylbiguanidnio-co-allylamine) | $(CH_2-CH)$ | amine | $(CH_2-CH)$ | biguanide | $CH_2$ |
| poly(allylcarbamoylguanidino-co-allylamine) | $(CH_2-CH)$ | amine | $(CH_2-CH)$ | Carbamoyl guanidine | $CH_2$ |
| polyvinylbiguanide | $(CH_2-CH)$ | Biguanide | $(CH_2-CH)$ | biguanide | absent |

The polymer used may comprise linear, branched or dendrimeric molecules. The polymer may comprise a combination of linear, branched or dendrimeric molecules. The polymer may comprise one or any combination of molecules of Formula 1a or Formula 1b, for example as described above.

For example, the polymer can comprise one or more of polyhexamethylene biguanide (PHMB), polyhexamethylene monoguanide (PHMG), polyethylene biguanide (PEB), polytetramethylene biguanide (PTMB) or polyethylene hexamethylene biguanide (PEHMB). Some examples are listed in table A and B.

Thus, the polymer may comprise homogeneous or heterogeneous mixtures of one or more of polyhexamethylene biguanide (PHMB), polyhexamethylene monoguanide (PHMG), polyethylene biguanide (PEB), polytetramethylene biguanide (PTMB), polyethylene hexamethylene biguanide (PEHMB), polymethylene biguanides (PMB), poly(allylbiguanidnio-co-allylamine), poly(N-vinylbiguanide), polyallybiguanide.

The most preferred polymer comprises polyhexamethylene biguanide (PHMB).

The relative quantities of first species to the second species may be generally equal with one another, or one species may be the more prominent species within the composition.

Various methods may be used to form the nanoparticles and it is envisaged that the nanoparticles will be formed as a polymer and antifungal agent complex. However, polymer nanoparticles may be independently formed and then incubated with the antifungal agent together or separately in any order. The antifungal agent may be absorbed or attached to the nanoparticles in such a way so as to retain the efficacy of the antifungal agent against the fungi and the penetration enhancing effects of the nanoparticles.

In one embodiment of the present invention, a usually systemically administered antifungal agent is present in a dosage amount within the composition that is less than the therapeutically effective systemic dose of the antifungal agent. The antifungal agent may comprise agents which are commonly administered orally. As the composition can more effectively administer the antifungal agent to the site of infection, the dosage can be reduced and this can reduce potential toxicological issues with some antifungal agents.

It will be apparent to the skilled addressee that the composition may further comprise one or more of the following components: buffers, excipients, binders, oils, solvents, water, emulsifiers, glycerin, antioxidants, preservatives and fragrances or any additional components usually found in medicaments, and in particular topical creams and ointments. Furthermore, the composition could be in a number of forms such as a paste or a suspension. The composition may be formulated for use with a spraying device or for use in conjunction with a micro-needle array delivery system. If a micro-needle array is employed then it may be incorporated into an adhesive patch.

For certain applications, the composition may additionally comprise a permeating agent so as to allow delivery of the antifungal agent to infected area. For example, urea can be used to allow the nanoparticles breach the nail of an individual suffering from a fungal nail infection where the infection is underneath or in the nail itself. Additionally, solvents such as ethanol may be employed so as to enable dissolution of one or more components of the composition, such as the antifungal agent, into solution.

The composition of the invention may also be administered intranasally or by inhalation and may be conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the composition, e.g. using a mixture of ethanol and the propellant as the solvent, which may additionally contain a lubricant, eg sorbitan trioleate. Capsules and cartridges (made, for example, from gelatin) for use in an inhaler or insufflator may be formulated to contain a powder mix of the composition of the invention and a suitable powder base such as lactose or starch.

Aerosol or dry powder formulations are preferably arranged so that each metered dose or "puff" contains at least 1 µg of the composition for delivery to the patient. It will be appreciated that the overall daily dose with an aerosol will vary from patient to patient, and may be administered in a single dose or, more usually, in divided doses throughout the day.

Alternatively, the composition of the invention can be administered in the form of a suppository or pessary, or they may be applied topically in the form of a lotion, solution, cream, ointment or dusting powder. The composition of the invention may also be transdermally administered, for example, by the use of a skin patch. They may also be administered by the ocular route, particularly for treating diseases of the eye.

For ophthalmic use, the composition of the invention can be formulated using nanoparticle systems or as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the composition of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The topical composition as herein above described can be used to treat a number of fungal infections. However, it is particularly suited to treat fungal nail infection, athlete's foot or other types of fungal skin infection/dermatophyte infections (such as ringworm of the groin (Tinea cruris), ringworm of the body (Tinea corporis), ringworm of the scalp (Tinea capitis), other "ringworm" type infections). The invention will also be suited to treating yeast infections such as, but not limited to, intertrigo, pityriasis versicolor, and thrush (*Candida albicans*). The fungal infection may comprise a dermatophytic infection. However, the present invention can also be used to treat or modulate yeast infections and/or colonisation.

The composition as herein above described may be for use in the treatment or management of a fungal infection. The treatment may be a topical treatment.

The composition may comprise polyhexamethylene biguanide and Terbinafine. Preferably, the composition comprises polyhexamethylene biguanide in the range of 0.1 to 0.5 mg/ml and Terbinafine in the range of 0.06 to 60 mg/ml. More preferably, the composition comprises polyhexamethylene biguanide in the range of 0.2 to 0.4 mg/ml and Terbinafine in the range of 0.06 to 6 mg/ml. Most preferably, the composition comprises up to about 0.3 mg/ml polyhexamethylene biguanide and up to about 0.1 mg/ml of Terbinafine.

In one embodiment of the present invention, there is provided a composition comprising a nanoparticulate complex of polyhexamethylene biguanide and Terbinafine for the treatment of a fungal infection.

In a further aspect of the present invention, there is provided a composition comprising a nanoparticulate combination of polyhexamethylene biguanide, an antifungal agent for the treatment of a fungal infection.

In accordance with a further aspect of the present invention, there is provided a topical composition comprising a nanoparticulate combination of polyhexamethylene biguanide, Terbinafine nanoparticle complex for the treatment of a fungal infection.

In accordance with a yet further aspect of the present invention, there is provided a method of producing a composition for the treatment of a fungal infection comprising mixing a polymer capable of forming nanoparticles with terbinafine under conditions suitable to allow the formation of nanoparticles, wherein the nanoparticles comprise particles in the range of 0.5 to 5 nm and/or 150 to 250 nm.

The method may involve the forming of nanoparticles into at least two distinct particle sizes groups comprising:
a) a first species in the range of 0.5 to 5 nm; and
b) a second species in the range of 150 to 250 nm.

The method may also involve the step of forming the nanoparticles under conditions suitable for forming particles in the range of 0.5 to 5 nm and/or in the range of 150 to 250 nm, or alternatively further processing the mixture so as to select only nanoparticles in the range of 0.5 to 5 nm and/or in the range of 150 to 250 nm. The method may also involve the step of forming the nanoparticles under conditions suitable for forming nanoparticles in the range of 0.5 to 5 nm and in the range of 150 to 250 nm, or alternatively further processing the mixture so as to select nanoparticles in the range of 05 to 5 nm and in the range of 150 to 250 nm. A number of techniques may be employed to further process the mixture so as to select the nanoparticles in the required size ranges, such as centrifugation, electrophoretic, chromatographic or filtration methods. The measurement of the size/diameter of the nanoparticles is preferably conducted using dynamic light scattering analysis.

The method may further comprise formulating the composition into a topical medicament.

Again, it will be apparent that the method will be employed to produce a composition as herein above described.

In a yet an additional aspect of the present invention, there is provided a combination of a composition comprising a polymer capable of forming nanoparticles and an antifungal agent and a micro-needle array for use in the treatment of a fungal nail infection. The micro-needle array may be incorporated into an adhesive patch. The micro-needles may be less than 2 mm in length. More preferably, the micro-needles are less than 1.5 mm in length. Most preferably, the micro-needles are less than 1 mm in length. Preferably, less than 500 μm of the micro-needles are inserted into the skin. More preferably, less than 400 μm of the micro-needles are inserted into the skin. Most preferably, about 300 to 200 μm of the micro-needs are inserted into the skin. Preferably, the micro-needles administer the composition to the dermis and/or epidermis.

DETAILED DESCRIPTION OF THE INVENTION

Embodiments of the present invention will now be described, by way of example only, with reference to the following experiments and accompanying figures, in which:

FIG. 5 is a graph showing the total amount of terbinafine passing through nails contained in Franz cells incubated at 32° C. in a humid atmosphere for 7 days. The following formulations (40 μl) were applied daily to the upper chamber of the Franz cells: 0.3 mg/ml PHMB+0.1 mg/ml terbinafine or 10 mg/ml terbinafine. The total dose of terbinafine used in each experiment was 4 μg or 400 μg respectively. The total amount of terbinafine passing through the nail combines the amount of terbinafine passing through the nails into a lower, water filled collection chamber of the Franz cells and the amount of terbinafine in ethanol washings of the underside of the nails. The total amount of terbinafine passing through the presented was calculated as the percentage of the total dose applied to the upper chamber. Tests were performed in triplicate;

FIG. 8 is a plan view diagram of a finger with a nail which is to be treated with a micro-needle patch for delivering the composition of the present invention;

The aim of the following experiments was to investigate whether cellular delivery of antifungals could be enhanced using a nanotechnology based delivery system with a cationic polymer Polyhexamethylene Biguanide (PHMB).

PHMB is an inexpensive, readily available disinfectant and antiseptic used commonly in dressings, swimming pools and contact lens solutions. It is believed that its antiseptic action works by disrupting cell membranes of organisms and thereby causing leakage of cell contents. The experiments also assessed the effects of different concentrations of an antifungal agent on fungal species to enable determination of suitable dosage levels.

Nanoparticle Formation with Terbinafine and PHMB

Experiments were conducted to form nanoparticles with Terbinafine and PHMB.

Terbinafine was mixed at 0.1 mg/ml in 30% ethanol and incubated at room temperature for at least 24 hours up to a maximum of 47 days. Another formulation was prepared by mixing terbinafine at 0.1 mg/ml in 30% ethanol and then adding PHMB to 0.3 mg/ml. The formulation was incubated at room temperature for at least 24 hours up to a maximum of 112 days. The number and size of any nanoparticles formed were measured using a Malvern Instruments Nanosight LM10.

Figure 1A:
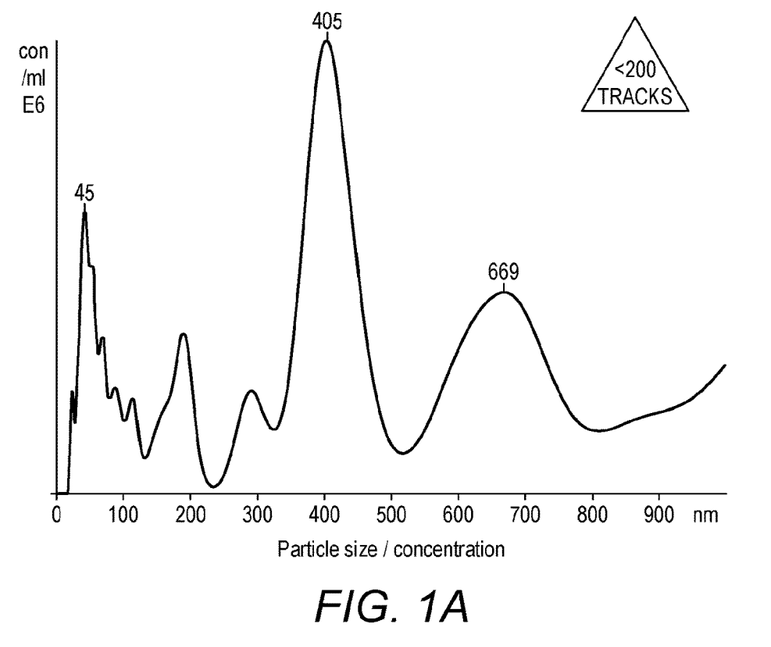
FIG. 1A is a graph showing the size distribution of particles formed by mixing 0.1 mg/ml terbinafine in 30% ethanol and incubating at room temperature for at least 24 hours. The particle size distribution was measured using Malvern Instruments Nanosight LM10 (particle size range=50-800 nm, particle number=$0.5 \times 10^8$ particles/ml)
Figure 1B:
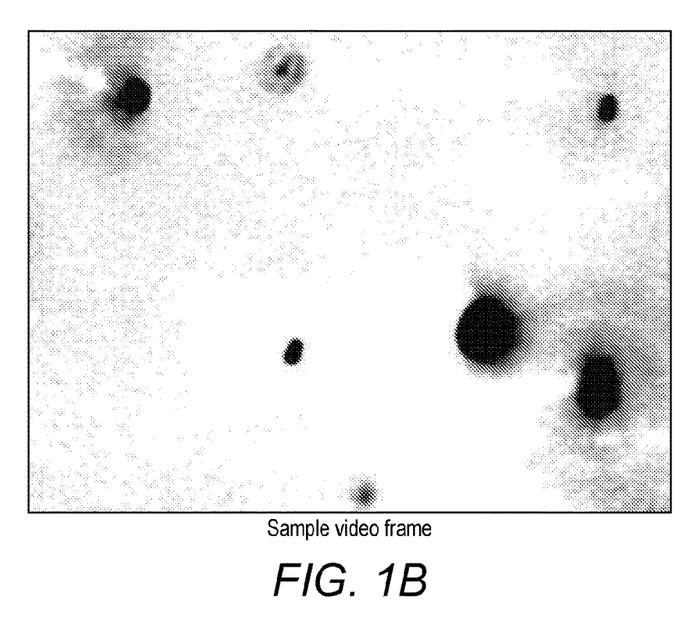
FIG. 1B is a video frame image of particles formed by mixing 0.1 mg/ml terbinafine in 30% ethanol and incubating at room temperature for at least 24 hours. The particles were visualised using Malvern Instruments Nanosight LM10.
Figure 2A:
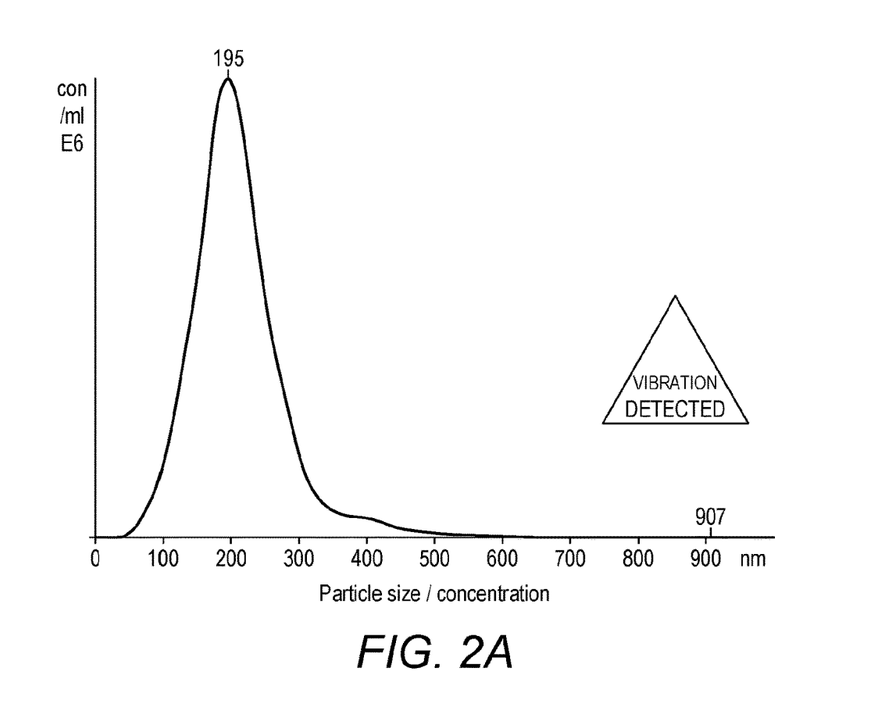
FIG. 2A is a graph showing the size distribution of particles formed by mixing 0.1 mg/ml terbinafine and 0.3 mg/ml PHMB in 30% ethanol and incubating at room temperature for at least 24 hours. The particle size distribution was measured using Malvern Instruments Nanosight LM10 (particle size range=100-300 nm, mode size=195 nm, particle number=$12 \times 10^8$ particles/ml)
Figure 2B:
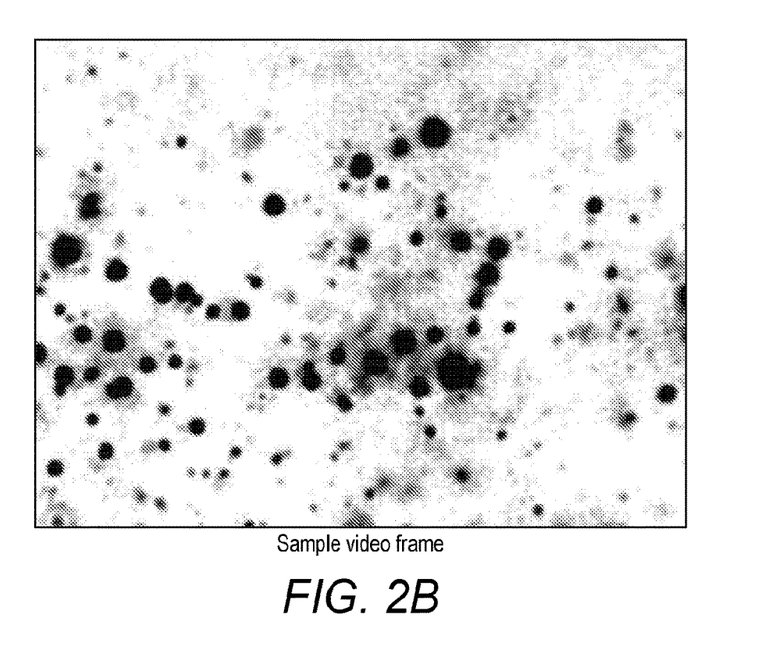
FIG. 2B is a video frame image of particles formed by mixing 0.1 mg/ml terbinafine and 0.3 mg/ml PHMB in 30% ethanol and incubating at room temperature for at least 24 hours. The particles were visualised using Malvern Instruments Nanosight LM10.

Approximately $0.5 \times 10^8$ particles/ml were formed when terbinafine alone was mixed in 30% ethanol. As shown in FIG. 1A the particle size ranged from 50 to 800 nm. Approximately $12 \times 10^8$ particles/ml were formed when terbinafine and PHMB were mixed in 30% ethanol. As shown in FIG. 2A the particle size ranged from 100 to 300 nm and had a mode size of 195 nm. FIGS. 1B and 2B are video frames from the Nanosight LM10 visualising the density and size of nanoparticles formed when terbinafine alone was mixed with 30% ethanol and when terbinafine and PHMB were mixed with 30% ethanol, respectively. The video frames show that the addition of PHMB to terbinafine and ethanol increased the number of particles formed and caused the formation of smaller nanoparticles.

Formulation of terbinafine with PHMB in 30% ethanol significantly increased the number of nanoparticles formed and resulted in the formation of more mono-disperse nanoparticles than the particles formed with terbinafine alone in 30% ethanol. The results showed that PHMB could be used to form mono-disperse nanoparticles with an antifungal agent which could then be used in the preparation of a topical medicament for the subsequent treatment of a range of potential fungal infections.

Analysis of Nanoparticles

Figure 3:
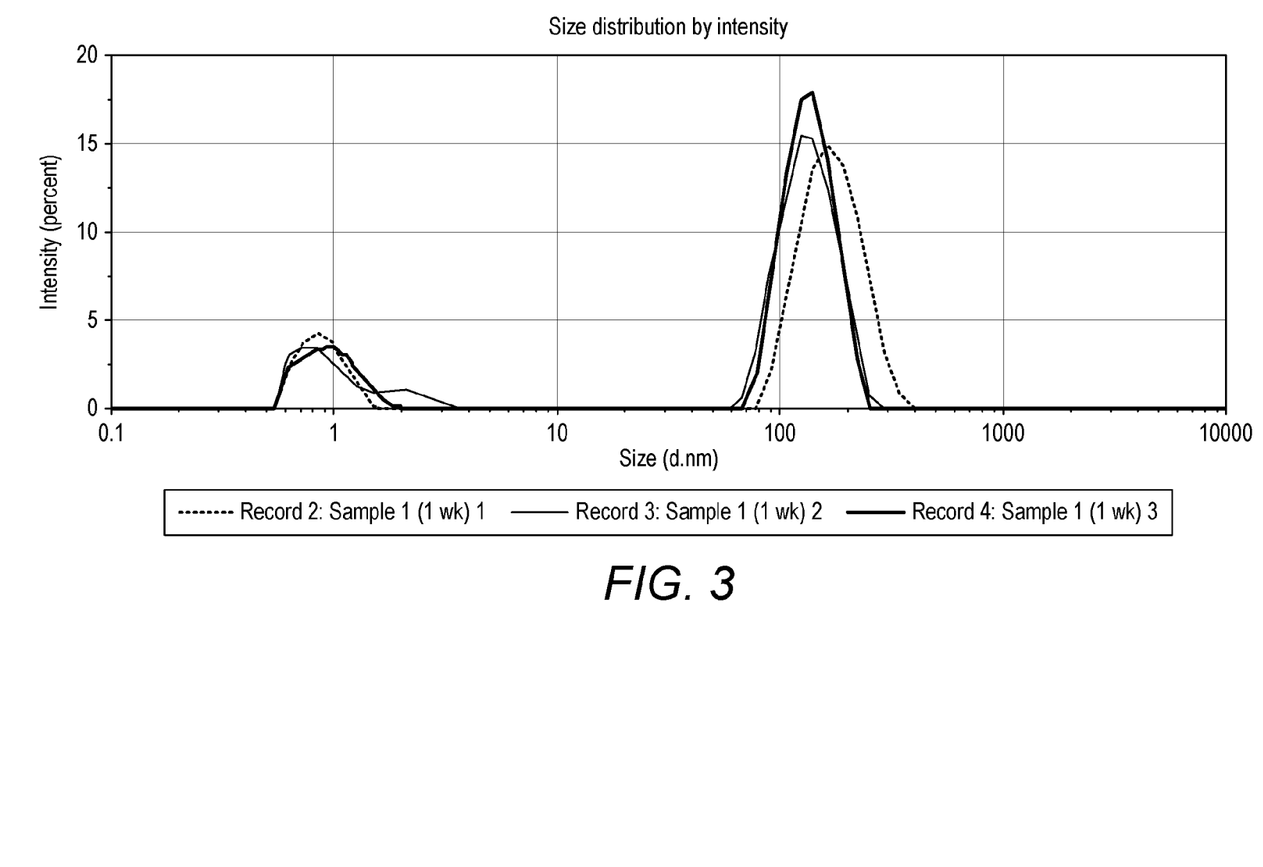
FIG. 3 is a graph showing the size distribution by intensity of the nanoparticles formed of 0.3 mg/ml PHMB/0.1 mg/ml terbinafine nanoparticles measured on a Malvern instruments Zetasizer.

The LM10 instrumentation has a lower limit of detection of 20 nm diameter. So formulations used in the drug delivery experiments were analysed using a Malvern Instruments Zetasizer, which is capable of detecting smaller nanoparticles formed FIG. 3 shows the analysis of 0.3 mg/ml PHMB/0.1 mg/ml terbinafine nanoparticles on a Malvern instruments Zetasizer. This instrument uses dynamic light scattering and can measure particle sizes down to 0.1 nm diameter. Note the appearance of the second species of nanoparticles around the 0.3-3 nm range in this analysis. The table below shows the results (Sample identifiers refer to the traces in FIG. 3). A polydispersity index threshold of <0.4 was used. The Z-average (particle diameter) of the major peak is in broad agreement with that observed on the LM10 instrument.

| Sample | Z-average (diameter nm) | Polydispersity index (Pdi) |
|---|---|---|
| Record 2: Sample 1 (1 wk)1 | 113.3 | 0.545 (Discounted as outside of tolerance) |
| Record 3: Sample 1 (1 wk)2 | 160.4 | 0.194 |
| Record 4: Sample 1 (1 wk)3 | 176.3 | 0.212 |

As can be seen, there are two distinct species of nanoparticles being formed: i) in the range of 0.5-3 nm; and ii) about 170 nm.

Franz Cells

Nail clippings were soaked in water overnight at 30° C. and dried briefly. A 3 mm diameter punch was used to take disc biopsies of the nail clippings. Each nail disc was added to a Franz cell and an upper chamber of the cell attached. 40 µl of the following formulations was added to the upper chambers: 0.3 mg/ml PHMB+0.1 mg/ml terbinafine; or 10 mg/ml terbinafine. Lower collection chambers of the Franz cells were filled with water (approximately 600 µl). The Franz cells were incubated at 32° C. in a humid atmosphere for 7 days. On day 7 the contents of the lower chambers were removed and the under sides of the nails were washed 5 times with 10 µl of 100% ethanol. The ethanol washings were retained for analysis.

Figure 4:
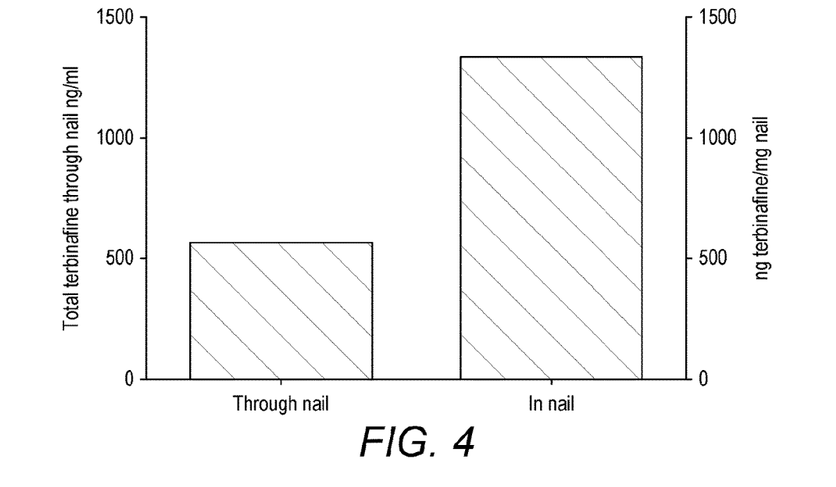
FIG. 4 is a graph showing the total amount of terbinafine passing through and remaining associated with the nails after 7 days incubation in Franz cells at 32° C. in a humid atmosphere following application of 40 μl of 0.3 mg/ml PHMB+0.1 mg/ml terbinafine to the upper chambers of the Franz cells. Tests were performed in duplicate.
Figure 5:
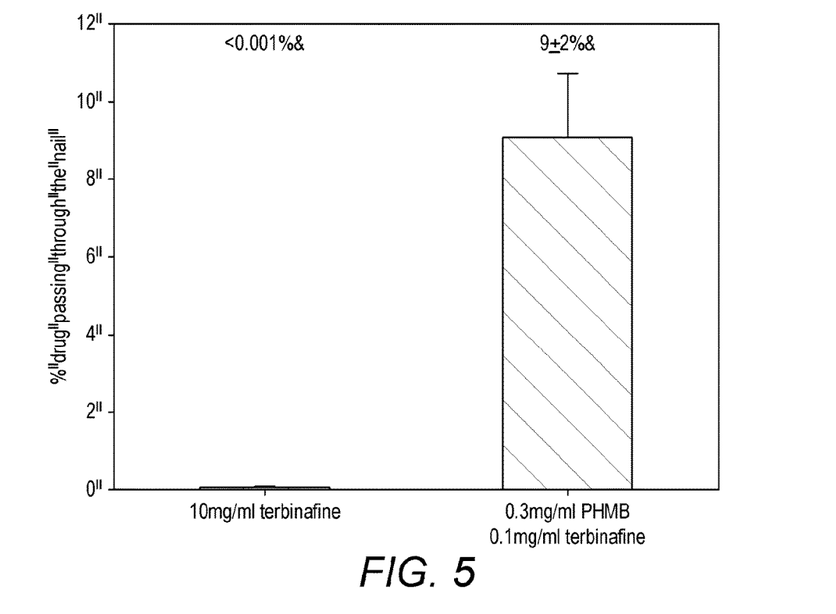

Total terbinafine penetration through the nails was determined by measuring the concentration of terbinafine in the water of the lower chambers and the terbinafine concentration in the ethanol washings of the nails. FIG. 4 compares the total amount of terbinafine passing through the nails and remaining within the nails when a 0.3 mg/ml PHMB:0.1 mg/ml terbinafine formulation was applied. The total concentration of terbinafine passing through the nail following 7 days of dosing was approximately 0.6 µg/ml. FIG. 5 shows that a 0.3 mg/ml PHMB:0.1 mg/ml terbinafine formulation resulted in a significant and substantial increase in penetration of terbinafine through the nail with approximately 10% of the dose being recovered in the lower chamber and ethanol washes of the underside of the nail. The results demonstrate the advantages of using PHMB in combination with terbinafine to enhance the penetration of the antifungal agent through nails.

Figure 6:
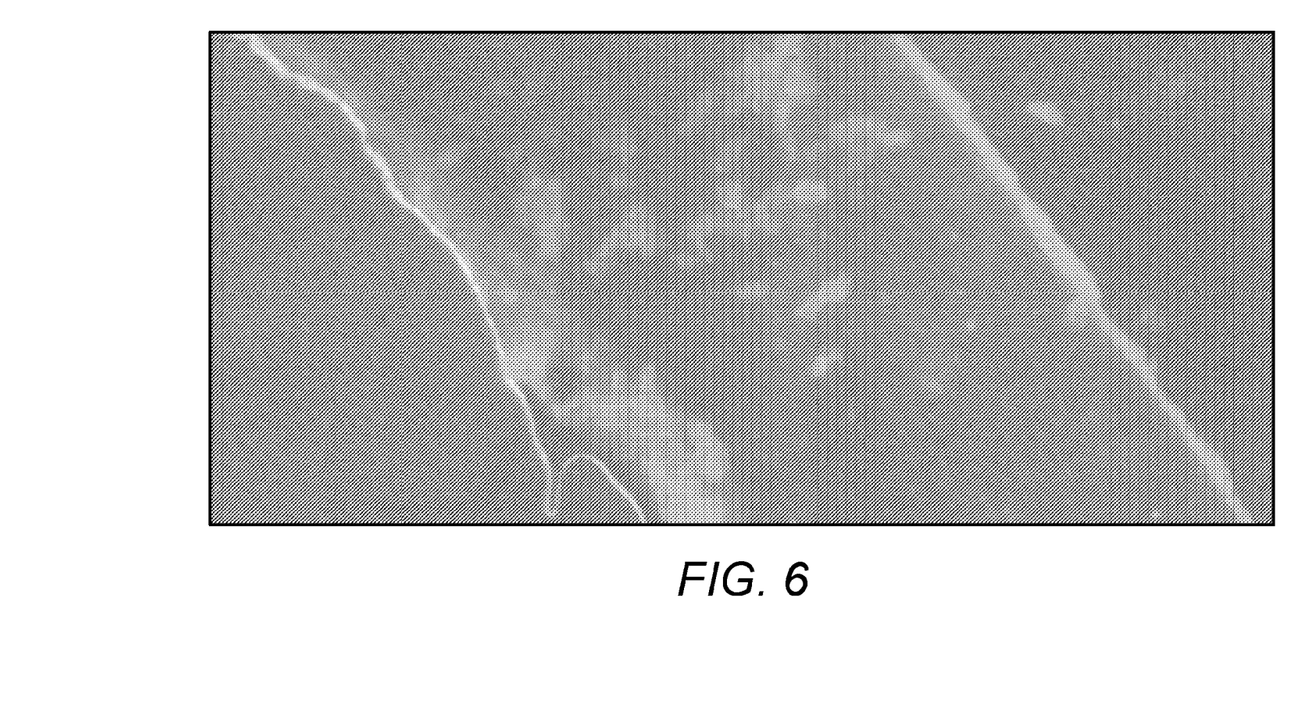
FIG. 6 is a photograph of a histological sample of a nail clipping from a healthy human volunteer which was soaked for 24 hours at 32° C. in a solution of 0.25 mg/ml PHMB, 0.05 mg/ml FITC labelled PHMB (1 in 5 spike of fluorescently labelled PHMB) and 0.1 mg/ml terbinafine.

FIG. 6 shows a sample nail clipping from a healthy human volunteer was soaked for 24 hours at 32° C. in a solution of 0.25 mg/ml PHMB, 0.05 mg/ml FITC labelled PHMB (1 in 5 spike of fluorescently labelled PHMB) and 0.1 mg/ml terbinafine. The nails were sectioned and then fluorescence measured on a fluorescent microscope. As can be seen from the image, the fluorescently labelled polymer can be detected within the nail section indicating that it has successfully penetrated into the nail sample.

Assessment of Antifungal Activity

The antifungal activity of a range of concentrations of terbinafine, encompassing the concentrations range passing through the nails in the Franz cells, was tested. Terbinafine was diluted to the following concentrations in double distilled water: 60, 6, 0.6 and 0.06 µg/ml. 40 µl of each terbinafine solution and double distilled water alone was spotted onto a 10 mm sterile 3 MM paper disk. Each disk was placed on a lawn of *Trychophyton mentagrophytes* plated on yeast extract peptone dextrose (YEPD) agar plates. *T. mentagrophytes* was used as a laboratory fungal strain due to its relevance to key pathogenic species in onychomycosis (fungal nail infection). The agar plates were inverted and incubated at 30° C. for 4 days. The plates were photographed and analysed for zones of clearance, which indicate antifungal activity.

Figure 7A:
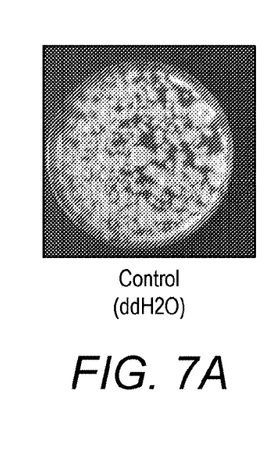
FIGS. 7A-7E are photographic images of yeast extract peptone dextrose (YEPD) agar plates with *Trychophyton mentagrophytes* after incubation for 4 days at 30° C. Each plate had a 10 mm sterile paper disk placed in the centre of the *T. mentagrophytes* lawn. 40 μl of double distilled water or terbinafine solution of varying concentration was spotted onto each paper disk. The concentration of the terbinafine solutions used were: 0 μg/ml (control, FIG. 7A), 0.06 μg/ml (FIG. 7B), 0.6 μg/ml (FIG. 7C), 6.00 μg/ml (FIG. 7D) and 60.0 μg/ml.
Figure 7B:
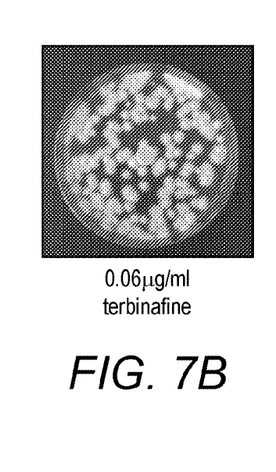
Figure 7C:
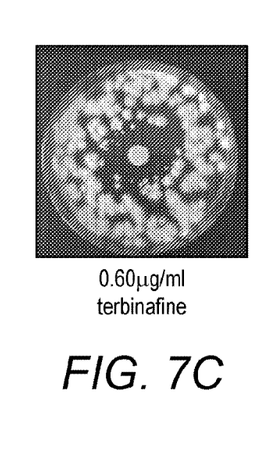
Figure 7D:
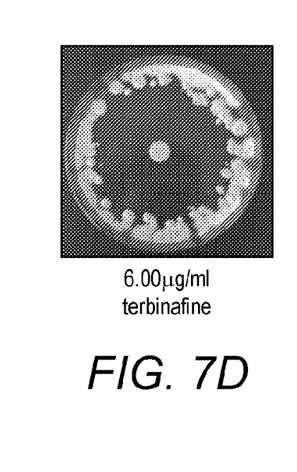
Figure 7E:
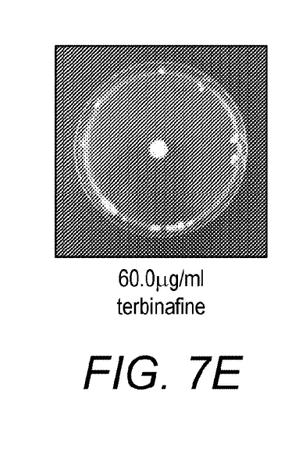

FIGS. 7A to 7E are photographic images showing the growth of *T. mentagrophytes* on the agar plates growth. FIG. 7A shows *T. mentagrophytes* on a control plate in the absence of terbinafine. FIG. 7B shows *T. mentagrophytes* in the presence of a paper disk imbibed with 40 µl of a 0.06 µg/ml terbinafine solution. There appears to be no zone of clearance surrounding the disk and therefore minimal or no inhibition of *T. mentagrophytes*. FIGS. 7C-E show *T. mentagrophytes* in the presence of a paper disks imbibed with 40 µl of a 0.6 µg/ml, 6 µg/ml and 60 µg/ml terbinafine solution, respectively. There are clear zones of clearance surrounding the paper disks indicating *T. mentagrophytes* growth has been inhibited by terbinafine at these concentrations.

The size of the zone of clearance surrounding the paper disks shows dependence on the concentration of terbinafine applied to each disk. The largest zone of clearance is seen for 60 μg/ml terbinafine solution. Progressively smaller zones of clearance are seen for 6 μg/ml and 0.6 μg/ml terbinafine solutions.

This experiment shows that the amount of terbinafine penetrating through nails over 7 days when a formulation of 0.3 mg/ml PHMB:0.1 mg/ml terbinafine is applied, which is approximately 0.6 μg/ml, is sufficient to provide effective antifungal action.

Effect of Storage on Nanoparticle Size and Number

A solution of terbinafine (100 ug/ml) and PHMB (300 ug/ml) was made in 30% (v/v) ethanol and stored in a clear polypropylene plastic tube under ambient laboratory conditions of temperature and light. Samples were removed from this solution on days 1, 7, 14, 21, 32, 39, 45, 53, 67, 99 and 112 and then analysed on the LM10 for nanoparticle size and number.

The results for mode particle size and number are in the below table:

| Day | Particle number | Mode particle size (nm) |
| --- | --- | --- |
| 1 | 2000000000 | 211 |
| 7 | 1280000000 | 195 |
| 14 | 1380000000 | 186 |
| 21 | 940000000 | 192 |
| 32 | 1152000000 | 167 |
| 39 | 770000000 | 174 |
| 45 | 1070000000 | 169 |
| 53 | 747000000 | 175 |
| 67 | 899000000 | 164 |
| 99 | 696000000 | 186 |
| 112 | 520000000 | 192 |

Figure 8A:
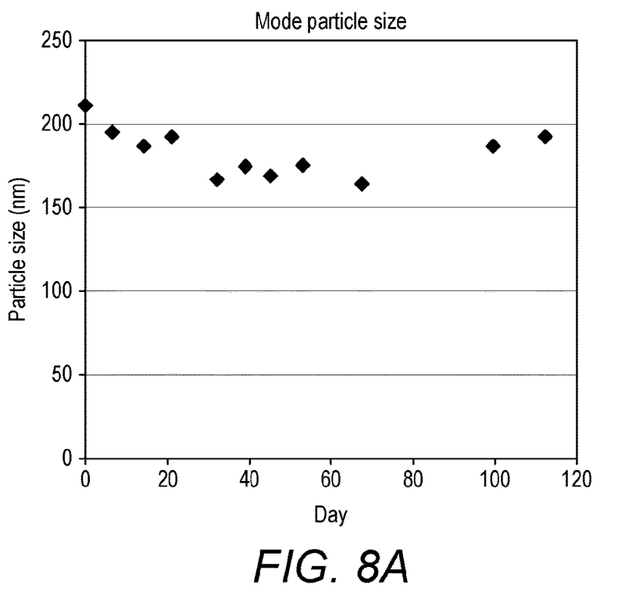
FIG. 8A is a graph showing the mode particle size of the terbinafine and PHMB nanoparticle composition over 120 days of storage.
Figure 8B:
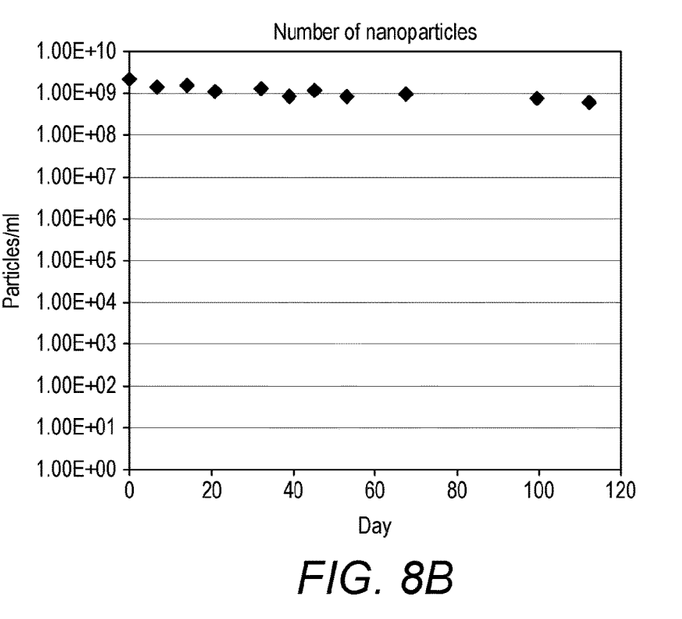
FIG. 8B is a graph showing the number of terbinafine and PHMB nanoparticles per ml over a 120 days of storage.

The mode of particle numbers and the numbers of particles per ml were also plotted against the day of sampling and are shown in the graphs of FIGS. 8A and 8B.

These experiments demonstrated that over time the mode of particle size was not constant but varied, but was generally, within the 150-200 nm range. More precisely, the average modal particle sizes of the larger species were found to be in the range of about 164 nm and about 211 nm from day 1 to day 112. Following an initial drop, the numbers of particles remained roughly constant.

Effect of Storage on Efficacy of Nanoparticles on *C. albicans*

Figure 9:
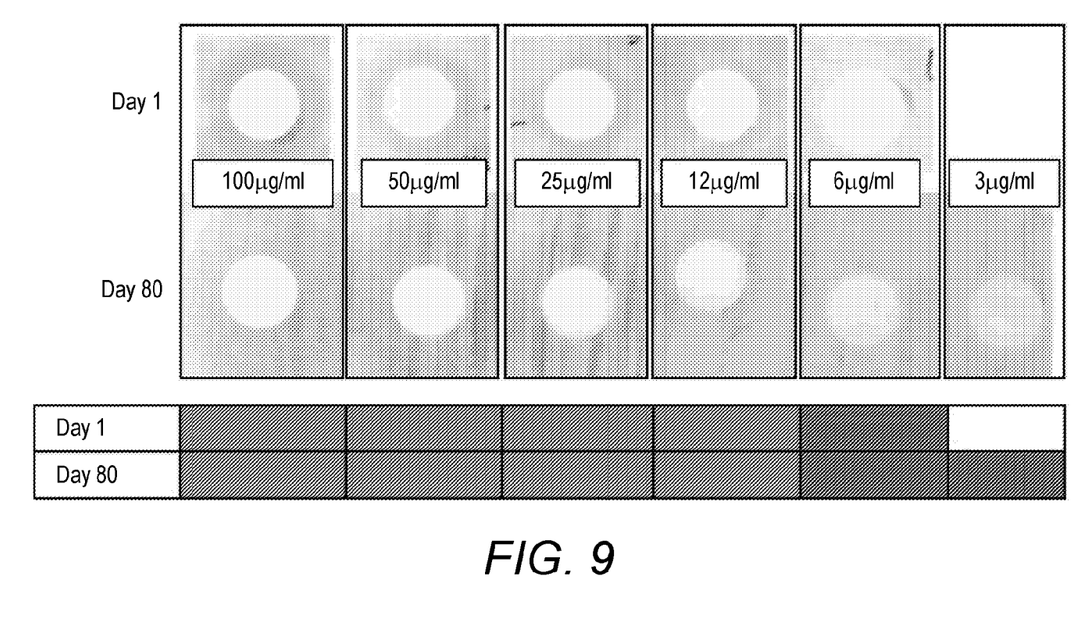
FIG. 9 are photographic images of sterile filter discs soaked in 100 to 3 μg of terbinafine on lawns of *Candida albicans* grown on YEPD agar plates at day 1 and 80 so as to confirm that the PHMB nanoparticle composition was still effective even after storage.

10 mm sterile filter paper disks were soaked in the dilutions of the stock solution used for the stability test made on Day 1 or when it had been stored under ambient room temperature and light conditions for 80 days (Day 80). The concentrations refer to the terbinafine concentration in the diluted solutions (100 μg/ml; 50 μg/ml; 25 μg/ml; 12 μg/ml; 6 μg/ml; and 3 μg/ml). The disks were laid onto lawns of *Candida albicans* grown on YEPD agar plates. Antimicrobial effects were directly visualized as zones of clearance around the paper disks and are shown in FIG. 9. The minimum inhibitory concentration (MIC) in this assay was defined as the minimum concentration of solution at which a clear zone of clearance was visible. The grid below the images of the disks indicates where zones of clearance were observed (dark grey=zone of clearance (100 μg/ml to 12 μg/ml at Day 1 and Day 80), light grey=no clearly defined zone of clearance (6 μg/ml to 3 μg/ml at Day 1 and Day 80). The MICs calculated on day 1 and day 80 were the same at 12 μg/ml.

The results of this assay show that the PHMB and terbinafine nanoparticles retained efficacy after storage of up to 80 days.

Micro-Needle Patch

Transdermal patches have long been used for the administration of small-molecule lipophilic drugs that can be readily absorbed through the skin. This non-invasive delivery route is advantageous for the administration of many drugs incompatible with oral delivery, as it allows for direct absorption of the drug into the systemic circulation, bypassing both the digestive and hepatic portal systems which can also dramatically reduce the bioavailability of many drugs. Transdermal delivery also overcomes many of the challenges associated with subcutaneous injection by greatly reducing patient discomfort, needle anxiety, risk of accidental needle stick injury to the administrator and issues surrounding sharps disposal.

Despite these many advantages, transdermal delivery of drugs is confined to classes of molecules compatible with absorption through the skin. Delivery of small molecule salts and therapeutic proteins are not typically viable with traditional transdermal delivery, as the skin provides an effective protective barrier to these molecules even in the presence of absorption-enhancing excipients. However, micro-needle technology can be employed to deliver the nanoparticles containing antifungal agents directly to the epidermis, dermis and the nail matrix (where the nail and skin meet at the eponychium). By delivering the composition of the invention in this way, the nanoparticles will enter the nail matrix and capillary system and deliver the antifungal nanoparticle composition to the nail bed, under the hard nail plate, and into the fungi. In this way the potent antifungal agents can be directly delivered to the site of action thus reducing the treatment time and enhancing the potency.

Figure 10:
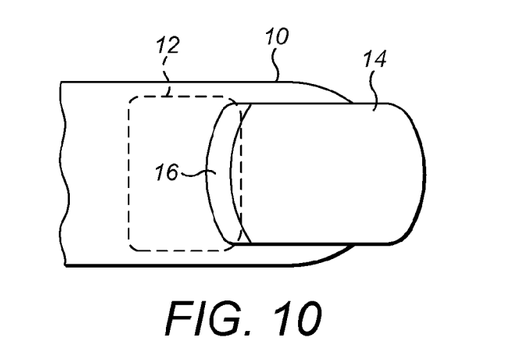
FIG. 10 is a plan view of a finger with a nail which is to be treated with a micro-needle patch for delivering the composition of the invention.
Figure 11:
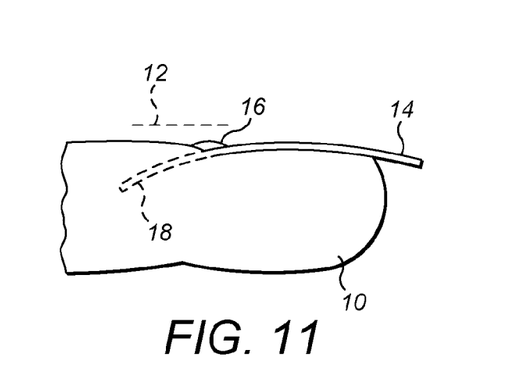
FIG. 11 is a cross-sectional diagram of a finger as shown in FIG. 10.

FIGS. 10 and 11 show diagrams of a finger 10 to which a micro-needle patch (illustrated in FIG. 12) can be applied to a finger within the treatment area 12 shown by a dotted line. The treatment area 12 is formed of the dermis behind the nail 14 and also at the nail matrix (eponychium) 16 where the nail and skin meet. The nail root 18 is located in the area under the dermis behind the nail and can therefore be treated effectively by applying a micro-needle patch for delivering the composition of the present invention. Of course, the micro-needle patch could be used for toe nails in addition to finger nails.

Figure 12:
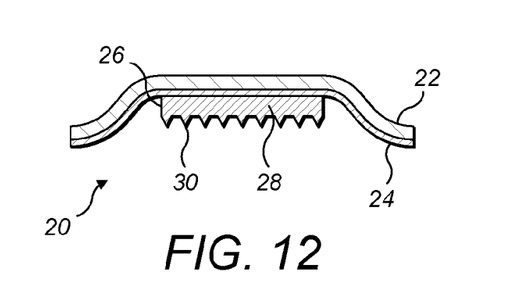
FIG. 12 is a cross-sectional diagram of a micro-needle patch.

FIG. 12 shows a diagram of a micro-needle patch which can be used to apply the composition of the present invention to an individual suffering from a fungal nail infection. The micro-needle patch 20 is formed of a flexible web of material 22 having an adhesive 24 applied to its underside. Centrally located on the underside of the flexible web is an array of downwardly extending micro-needles 26 having a plurality of points 30. The points can be formed as needles having conduits which are connected to a reservoir 28 containing the composition or simply have their points coated in the composition. In an alternative configuration, a reservoir 28 can expel the composition through holes disposed about the micro-needle arrays so that the composition can continuously coat the points of the array over a predetermined time frame. It will be apparent to the skilled addressee that a number of different micro-needle patches are currently available and that the composition of the present invention could be adapted for use with a range of them.

The micro-needles, can be less than 2 mm in length, and preferably about 250 μm will be inserted into the skin with minimum patient discomfort and, given the small hole created, with minimal risk of post-injection infection, bleeding, or risk of inadvertent IV injection for an intradermal administration. In addition, micro-needles reduce risk to the injection administrator, as accidental puncture of the skin is nearly impossible with these small projections.

It is envisaged that the micro-needle patch could be used for a single treatment where all the patient has to do is remove the patch from a wrapper and apply it to the appropriate part of the finger or toe for a given period of time. In the alternative, the micro-needle patch could be sold in combination with the composition and the patient would coat a quantity of the composition onto the surface of the micro-needles and apply the patch to the body in the prescribed manner. The patch could come with markings on its exterior so as to assist the patient or physician correctly line up the micro-needles with the correct location on the finger or toe to be treated.

The forgoing embodiments are not intended to limit the scope of the protection afforded by the claims, but rather to describe examples of how the invention may be put into practice.

The invention claimed is:

1. A composition comprising nanoparticles formed of a polymer and terbinafine, said nanoparticles consisting of two particle size species, wherein
 the first species is in the range of 0.5 to 5 nm; and
 the second species is in the range of 150 to 250 nm, and
  wherein the polymer comprises polyhexamethylene biguanide.

2. A composition as claimed in claim 1, wherein the nanoparticles are formed with and/or in the presence of terbinafine.

3. A composition as claimed in claim 1, wherein the composition further comprises one or more of the following component(s): buffers, excipients, solvents, binders, oils, water, emulsifiers, glycerin, antioxidants, preservatives and fragrances.

4. A composition as claimed in claim 3, wherein the composition further comprises urea, ethanol, or both.

5. A composition as claimed in claim 1, wherein the terbinafine is present in a dosage amount within the composition, which is less than the therapeutically effective systemic dose of the antifungal agent.

6. A composition as claimed in claim 1, wherein the composition comprises polyhexamethylene biguanide in the range of 0.2 to 0.4 mg/ml and Terbinafine in the range of 0.06 to 6 mg/ml.

7. A composition as claimed in claim 1, wherein the composition is in the form of a cream, ointment, spray or powder.

8. A method of treating or managing a fungal infection, comprising administering the composition of claim 1.

9. A method as claimed in claim 8, wherein the treatment is topical.

10. A method as claimed in claim 8, wherein the fungal infection comprises a fungal nail infection, athlete's foot or a fungal skin infection.

11. A method as claimed in claim 8, wherein the fungal infection comprises a dermatophytic and/or yeast infection.

12. A method as claimed in claim 8, wherein the composition is administered by or in conjunction with a micro-needle array.

13. A method as claimed in claim 12, wherein the micro-needle array is incorporated into an adhesive patch.

14. A method of producing a composition for the treatment of a fungal infection comprising mixing a polymer capable of forming nanoparticles with terbinafine under conditions suitable to allow the formation of nanoparticles, wherein:
 a) the nanoparticles are formed under conditions to enable production of nanoparticles in the range of 0.5 to 5 nm and in the range of 150 to 250 nm; or
 b) the mixture is further processed so as to only select those nanoparticles in the range of 0.5 to 5 nm and in the range of 150 to 250 nm, and
 wherein the nanoparticles are formed or processed into two distinct particle sizes groups comprising:
  i) a first species in the range of 0.5 to 5 nm; and
  ii) a second species in the range of 50 to 250 nm,
 and wherein the polymer comprises polyhexamethylene biguanide.

15. A method as claimed in claim 14, wherein the method further comprises formulating the composition into a topical medicament.

16. A method of producing the composition as claimed in claim 1 comprising mixing a polymer capable of forming nanoparticles with terbinafine under conditions suitable to allow the formation of nanoparticles, wherein:
 a) the nanoparticles are formed under conditions to enable production of nanoparticles in the range of 0.5 to 5 nm and in the range of 150 to 250 nm; or
 b) the mixture is further processed so as to only select those nanoparticles in the range of 0.5 to 5 nm and in the range of 150 to 250 nm, and
 wherein the nanoparticles are formed or processed into two distinct particle sizes groups comprising:
  i) a first species in the range of 0.5 to 5 nm; and
  ii) a second species in the range of 50 to 250 nm.

* * * * *

UNITED STATES PATENT AND TRADEMARK OFFICE
CERTIFICATE OF CORRECTION

PATENT NO. : 10,517,835 B2
APPLICATION NO. : 15/741924
DATED : December 31, 2019
INVENTOR(S) : John Ridden, Christine Caroline Ridden and David Cook Page 1 of 1

It is certified that error appears in the above-identified patent and that said Letters Patent is hereby corrected as shown below:

On the Title Page

The Assignee (item (73)) should read:
"Blueberry Therapeutics Limited,"

Signed and Sealed this
Fourth Day of February, 2020

Andrei Iancu
*Director of the United States Patent and Trademark Office*